United States Patent [19]

Costello, Jr.

[11] Patent Number: 5,027,641
[45] Date of Patent: Jul. 2, 1991

[54] OSCILLOMETRIC NON-INVASIVE BLOOD PRESSURE SIMULATOR

[76] Inventor: Leo F. Costello, Jr., 900 Mix Ave., Unit 110, Hamden, Conn. 06514

[21] Appl. No.: 520,084

[22] Filed: May 7, 1990

Related U.S. Application Data

[63] Continuation of Ser. No. 314,566, Feb. 23, 1989, abandoned.

[51] Int. Cl.$^5$ ............................................. G01L 27/00
[52] U.S. Cl. ..................................................... 73/4 R
[58] Field of Search .............. 73/4 R, 865.6; 128/681; 434/268; 364/571.07, 578

[56] References Cited

U.S. PATENT DOCUMENTS 3,045,470 7/1962 Crandell et al. .
3,868,844 3/1975 Klein .
4,189,936 2/1980 Ellis .
4,464,123 8/1984 Glover et al. .
4,471,646 9/1984 Walker .
4,832,039 5/1989 Perry et al. .......................... 128/682

OTHER PUBLICATIONS

Biotek Product Literature-Blood Pressure Systems Calibrator Model 601A, Indirect Measurement in Man, pp. 86-99. Brochure-Critikon Dinamap Vital Signs Monitor OG, Apr. 9, 1968, U.S. Pat. No. 3,376,660.

Primary Examiner—Robert Raevis
Attorney, Agent, or Firm—Fishman, Dionne & Cantor

[57] ABSTRACT

An apparatus for evaluating the performance characteristics of an oscillometric blood pressure monitor is presented. In accordance with the present invention, a novel closed-loop system is used to synthesize physiologically-correct pneumatic pulse waveforms and oscillometric envelopes in order to allow dynamic performance evaluation of any oscillometric monitor, regardless of manufacturer.

15 Claims, 6 Drawing Sheets

OSCILLOMETRIC NON-INVASIVE BLOOD PRESSURE SIMULATOR

This is a continuation of application Ser. No. 314,566, filed on Feb. 23, 1989, now abandoned.

BACKGROUND OF THE INVENTION

This invention relates generally to the field of automated measurement of blood pressure by the oscillometric method. More particularly, this invention relates to a method and apparatus for evaluating and testing the performance characteristics of oscillometric blood pressure monitors and associated cuff.

Oscillometry has become the preferred method for non-invasive blood pressure (NIBP) monitoring. Oscillometric NIBP monitors (oscillometers) are widely used in the Operating Room, and are increasingly used as an alternative to invasive monitoring in the Intensive Care Unit and Coronary Care Unit.

Commercially available oscillometric monitors have proprietary algorithms for predicting the mean, systolic and diastolic pressure from the oscillometric envelope. The more advanced monitors also use complex algorithms intended to reduce noise such as motion artifact. However, no systematic, standardized method is available to evaluate the efficiency of these new devices and algorithms. Static calibration does not test dynamic functionality, human subject comparisons are unreliable and clinical studies are not suitable for routine calibration and performance verification.

U.S. Pat. No. 4,464,123 to Glover et al describes a device for evaluating oscillometers. However, the oscillometer evaluator of the Glover et al patent is capable only of evaluating a specific line of oscillometers manufactured by a specific company under a very specific and artificial set of conditions. The Glover et al device may not yield meaningful test data for oscillometers manufactured by other companies.

U.S. Pat. No. 4,189,936 to Ellis discloses a device for testing invasive blood pressure monitors as opposed to non-invasive oscillometers.

SUMMARY OF THE INVENTION

The above-discussed deficiencies and other drawbacks of the prior art are overcome or alleviated by the method and apparatus of the present invention for evaluating the performance characteristics of an oscillometric blood pressure monitor. In accordance with the present invention, a novel closed-loop system is utilized to synthesize physiologically-correct pneumatic pulse waveforms and oscillatory envelopes in order to allow dynamic performance evaluation of any oscillometric monitor, regardless of manufacturer.

The present invention comprises a non-invasive blood pressure simulator which includes a cylindrical housing for receiving the cuff from the oscillometer to be tested. The housing encloses a pulse waveform synthesizer which generates a desired continuous electrical analog pulse waveform which is fed to a pneumatic or hydraulic pulse generator. A pressure transducer then senses the cuff pressure.

An important feature of the present invention is a servo loop for maintaining correct signals. This servo loop comprises a high pass filter and an error amplifier wherein the cuff pressure at a pressure transducer in the oscillometer is sensed by the pressure transducer in the simulator and its DC or steady state component is stripped away by the high pass filter; and its AC component is fed back to the error amplifier. The error amplifier compares the desired pulse waveform with the actual waveform and drives the pulse generator with a correction signal.

The above discussed and other features and advantages of the present invention will be appreciated and understood by those of ordinary skill in the art from the following detailed description and drawings.

BRIEF DESCRIPTION OF THE DRAWINGS

Referring now to the drawings, wherein like elements are numbered alike in the several FIGURES.

DESCRIPTION OF THE PREFERRED EMBODIMENT

Figure 1:
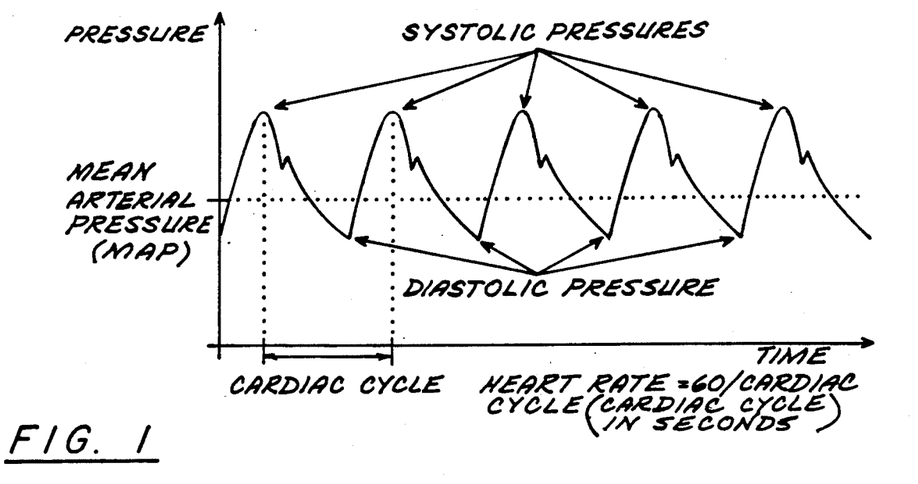
FIG. 1 is a graphical depiction of blood pressure (BP) versus time.

Prior to describing the structural details of the present invention, a brief discussion of non-invasive blood pressure monitoring, particularly monitoring using oscillometry techniques now follows. With reference first to FIG. 1, the arterial blood pressure waveform has four parameters that are of clinical interest:

1) The diastolic pressure is the minimum pressure during a single beat (cardiac cycle).
2) The mean arterial pressure (MAP) is the average pressure during a single cardiac cycle.
3) The systolic pressure is the maximum pressure during a single cardiac cycle.
4) The heart rate, in beats per minute, can be computed from the time interval, or period, from one cardiac cycle to the next.

Note that, in general, all four parameters will vary on a beat-to-beat basis.

These four arterial blood pressure parameters may be measured indirectly by the auscultatory method (the familiar procedure that uses a stethoscope and arm cuff), the ultrasound method (an ultrasonic blood flow detector replaces the stethoscope) and the oscillometric method. The first two methods, auscultatory and ultrasound, measure only the diastolic and systolic pressures. The latter method, oscillometry, actually measures only the mean arterial pressure, and estimates the systolic and diastolic pressures, as will be discussed below. All three methods measure the heart rate.

Oscillometry employs an occluding cuff identical to that used by nurses when manually taking a subject's blood pressure by the auscultatary method. However, unlike the auscultatary procedure, oscillometry determines the blood pressure entirely from the cuff pressure without the need for other patent sensors such as a stethoscope, microphone or ultrasound probe.

Figure 2:
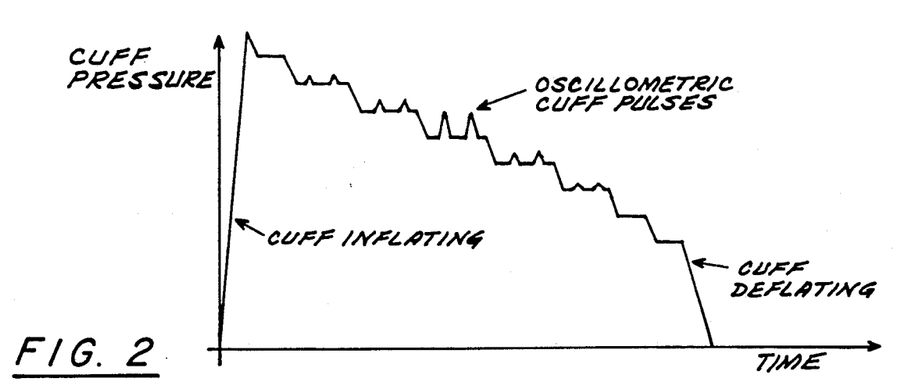
FIG. 2 is a graphical depiction of cuff pressure versus time as measured by an oscillometric blood pressure monitor.

FIG. 2 illustrates a time plot of the cuff pressure obtained during a typical oscillometric measurement cycle. The cuff is inflated above the subject's systolic pressure and then step-wise decreased below the diastolic pressure. When the cuff pressure is decreased to some pressure close to but still greater than the systolic pressure, each heartbeat will superimpose a pulse (or oscillation) on the cuff pressure. As the cuff pressure is decreased to the mean pressure, the pulses gradually increase to a maximum. As the cuff pressure is further decreased past the diastolic, the pulses gradually grow smaller and eventually disappear altogether.

Figure 3:
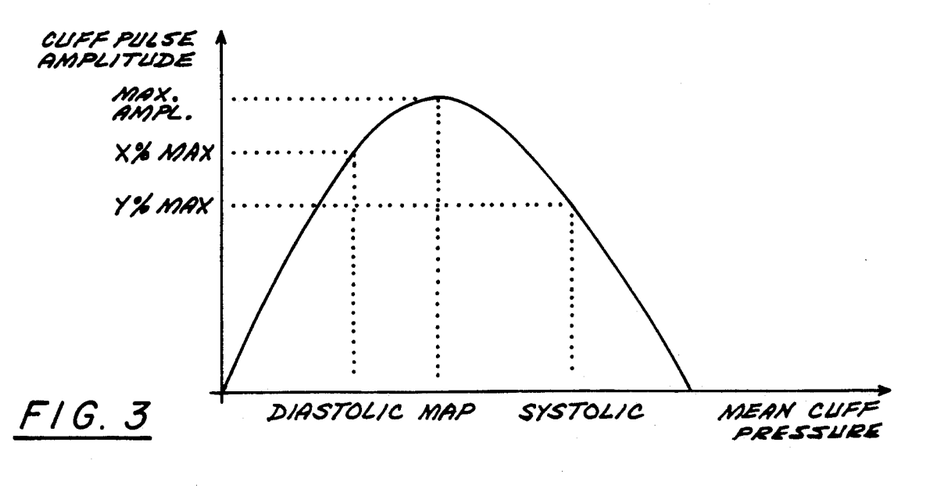
FIG. 3 is a graphical depiction of cuff pulse amplitude versus mean cuff pressure as measured by an oscillometric blood pressure monitor.

FIG. 3 shows these pulse amplitudes plotted against the mean cuff pressure at which they occurred. This plot is known as the oscillometric envelope. Clinical studies and theoretical investigations have established that the maximum pulse amplitude usually occurs at the mean blood pressure. Thus, to measure the MAP, oscillometric blood pressure instruments record this oscillometric curve, determine its maximum and read the corresponding cuff pressure.

In contrast, systolic and diastolic pressures are derived from the oscillometric envelope in a much less exact manner. In all oscillometric monitors commercially available at present, this is done by looking up the pressures above and below the mean at fixed relations of the maximum amplitude. No precise relationship between the systolic and diastolic pressures and the mean has been established. As a result, new oscillometric monitor designs are empirically "calibrated" to determine the best relationship. In fact, procedures which are based upon the derivative of the oscillometric envelope instead of the fixed fractional relations have been proposed as offering greater accuracy.

Aside from the systolic and diastolic pressures accuracy problem, the other practical problem with oscillometry is the reliable detection of the cuff pressure pulses. Noise can be introduced into the cuff pressure from, for example, arm motion or vibrations (in an ambulance or helicopter). Oscillometer manufacturers employ a variety of proprietary pulse detection algorithms to reject or cancel such noise.

The present invention comprises a simulator which interacts with the BP monitor it is testing (the "monitor-under-test") so as to generate oscillometric pulse waveforms and an oscillometric pulse-amplitude envelope that are standardized, repeatable and physiologically correct. An important feature of the simulator of the present invention is that it is suitable for use with oscillometers from any manufacturer. The MAP, systolic BP, diastolic BP and heart rate are "encoded" in the oscillometric envelope pattern. Thus, the user can select these four parameters and the present invention will synthesize cuff pulses whose amplitudes define an envelope corresponding to the selected blood pressures and whose spacing yields the selected heart rate. The measurements obtained by the monitor-under-test can then be compared to the known true values.

Figure 6:
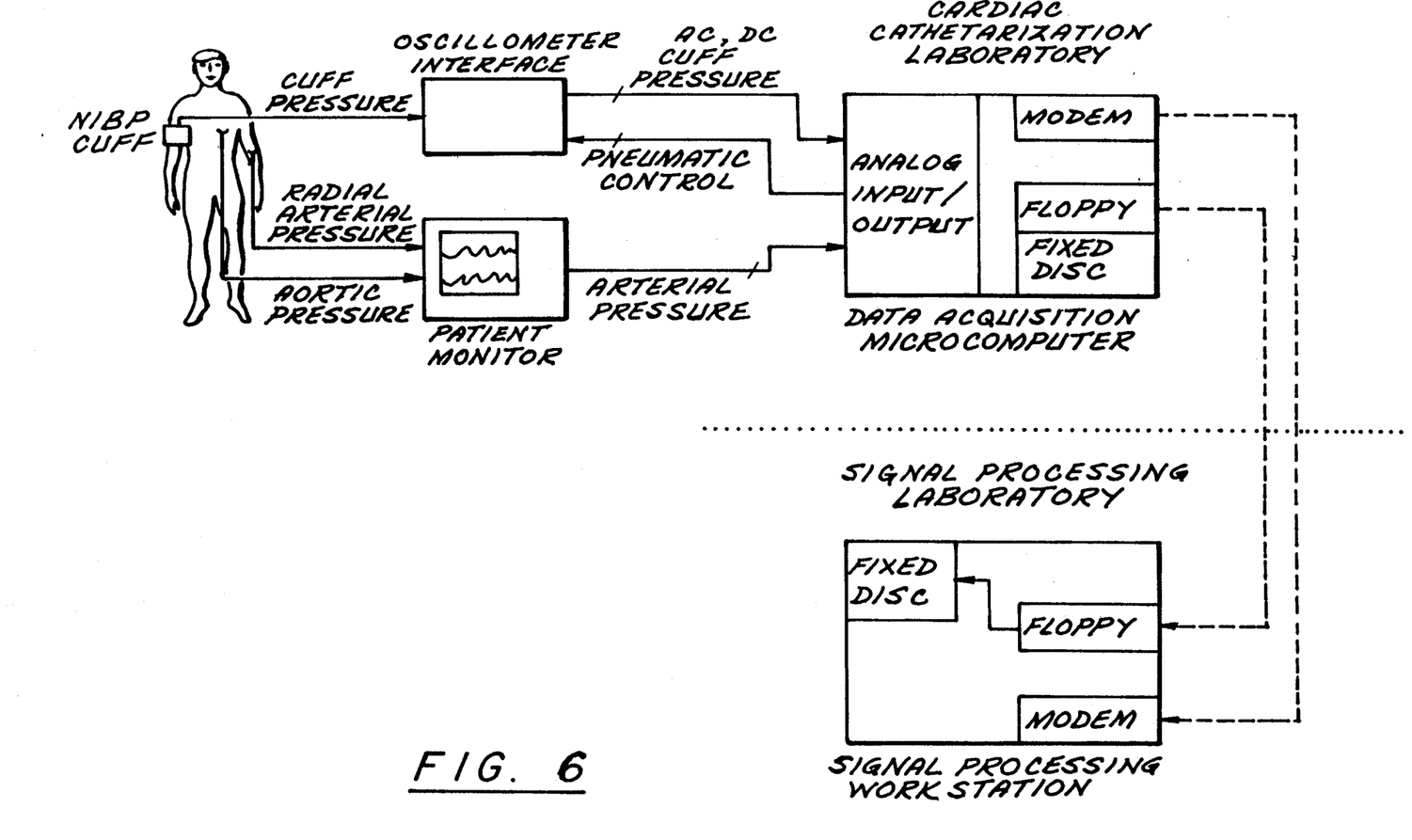
FIG. 6 is a block diagram of a typical clinical data collection set-up for obtaining physiologically correct BP waveforms.

The shape of the synthesized pulses and envelope, the pulse periods and the values for the MAP, systolic and diastolic pressures are all based upon a database obtained from clinical studies of the populations at large (see discussion of FIGURE 6). Thus, the monitor-under-test will receive physiologically-correct signals.

Figure 4:
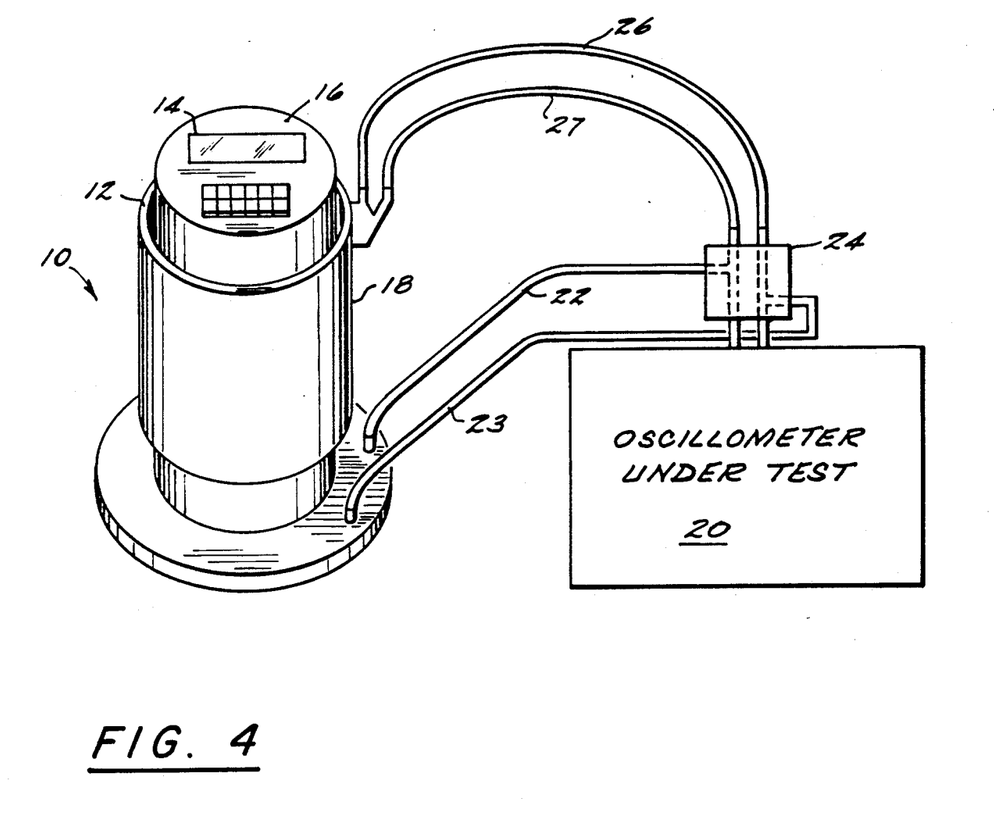
FIG. 4 is a perspective view of a non-invasive blood pressure simulator in accordance with the present invention shown connected to an oscillometer to be measured.

FIG. 4 depicts a preferred embodiment of the NIBP simulator of this invention. The simulator 10 is housed in a cylindrical enclosure 12 with a control console 14 (containing switches and an alphanumeric readout) on the top face 16 of enclosure 12. The cylindrical shape of closure 12 provides a convenient post for wrapping an arm cuff 18 from an oscillometer 20 to be tested. A pair of tubes 22 and 23 extending from the base of cylindrical enclosure 12 allows simulator 10 to interconnect with the oscillometric monitor 20 to be tested. A "T" fitting 24 at the monitor end of tubes 22 and 23 is plugged into the tubing receptacle at the rear of monitor 20. Tubes 22 and 23 are then plugged into fitting 24. A pair of second and third tubes 26 and 27 are connected between fitting 24 and cuff 18. "T" fitting 24 allows monitor 20 to communicate with arm cuff 18 and also allows simulator 10 access to the cuff pressure.

Figure 5A:
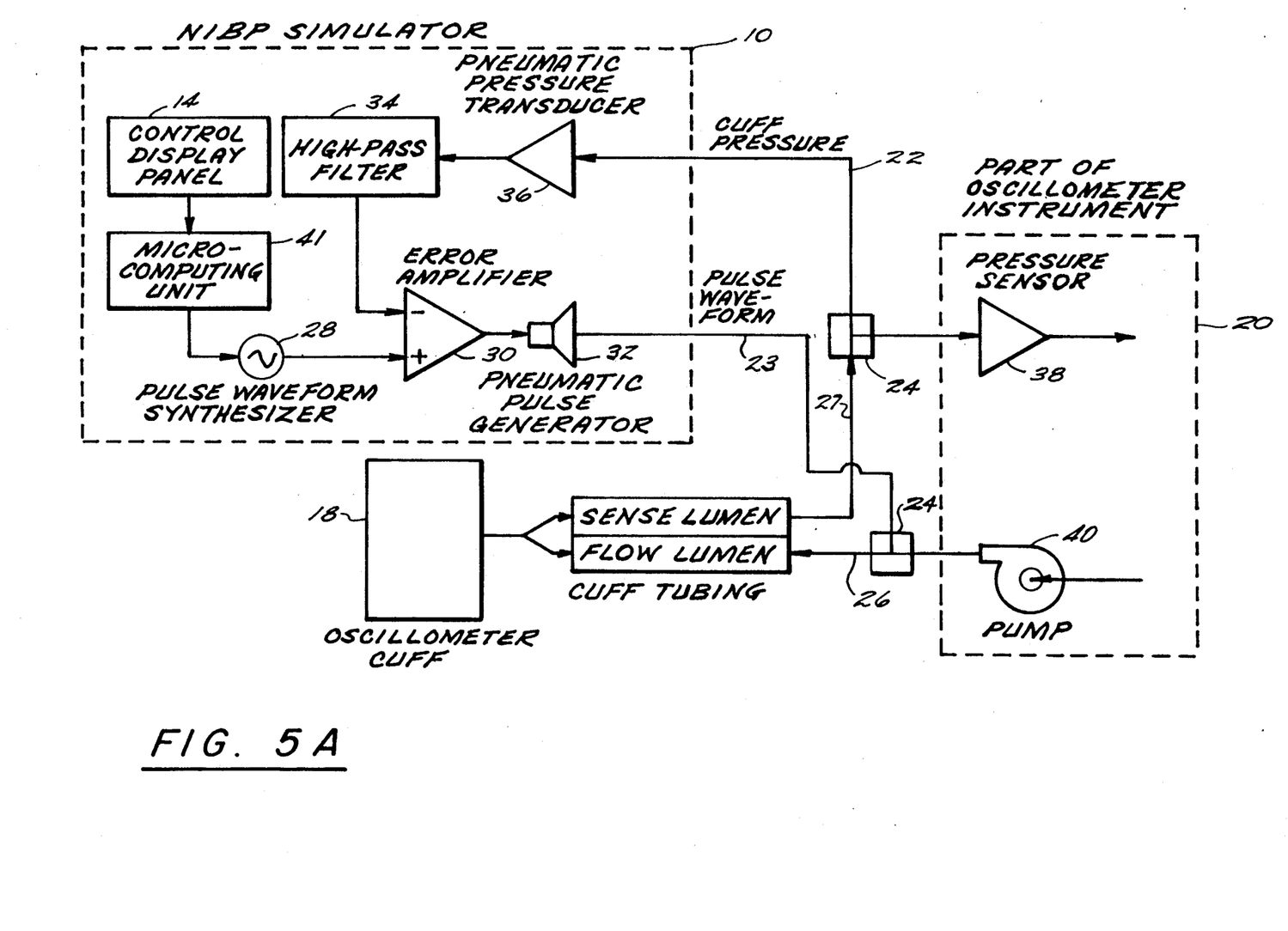
FIG. 5A is a schematic of the assembly of FIG. 4.

FIG. 5A is a block diagram of a preferred embodiment of simulator 10 with an attached monitor-under-test 20. Simulator 10 comprises a pulse waveform synthesizer 28, an error amplifier 30, a pneumatic pulse generator 32, a high pass filter 34 and a pneumatic pressure transducer 36. Simulator 10 also includes the pair of tubes 22 and 23 and fitting 24. A micro computing unit 41 delivers control information to the pulse waveform synthesizer 28 from control display unit 14. (Note however, that micro computing unit 41 may be an integral part of pulse waveform synthesizer 28). The known monitor-under-test components include a pressure transducer or sensor 38, a fluid pump 40, the oscillometer cuff 18 and the cuff tubing 26 and 27. Note that a dual lumen tube constitute the cuff tubing 26 and 27 with a flow lumen for connecting the pump to the cuff, and a sense lumen for connecting the cuff to the pressure sensor. Tubing 22 interconnects fitting 24 with pneumatic pressure transducer 36 and acts to deliver the cuff pressure to the simulator 10. Tubing 23 interconnects fitting 24 with pneumatic pulse generator 32 and acts to deliver the pulse waveform to oscillometer 20. In the interest of clarity, a substantial portion of the monitor-under-test, such as pneumatic valves and control and signal processing functions are not shown. However, such monitors are well known and are disclosed in detail in, for example, U.S. Pat. No. 4,349,034.

The components function as follows: The microcomputing unit 41 delivers to pulse waveform synthesizer (PWS) 28 numerical samples of the desired pulse waveform. PWS 28 then converts these numbers into a continuous electrical analog of the desired. waveform. Assuming for the moment that the feedback from the high pass filter (HPF) 34 is zero, pneumatic pulse generator (PPG) 32 is driven by, in effect, the output of PWS 28. PPG 32 then converts this electrical analog into the desired pneumatic signal.

Because of non-linearities in PPG 32, or unpredictable loading by the oscillometer cuff and tubing, the actual pneumatic pulse waveform arriving at oscillometer pressure sensor 38 may deviate from the desired waveform. In anticipation of this, the cuff pressure at pressure sensor 38 is sensed by pneumatic pressure transducer 36 and its "DC" or steady-state component is stripped away by HPF 34 and its "AC" component is fed back to error amplifier 30. Error amplifier 30 compares the desired pulse waveform with the actual and drives PPG 32 with a correction signal thus defining a servo loop.

The "servo loop" just described is an important feature of the present invention since electromechanical transducers (such as PPG 32) are well known for nonlinearities and difficulties in maintaining precision over time.

Two factors in particular will likely contribute to distortion of the desired pulse shape:
1) The mean, or DC, cuff pressure may vary from 30 mmHg to almost 300 mmHg. PPG 32 is directly exposed to this pressure; so it must superimpose the pulse waveform on top of it.
2) PPG 32 is operating under a load that is beyond control of the simulator system. Since simulator 10 is a universal device suitable for testing oscillometric monitors from many different manufacturers, variation in the properties (compliance and stiffness) of the oscillometer cuff and tubing must be allowed for.

Aside from PPG 32, the electronic components depicted in simulator 10 of FIG. 5A are all well known and commercially available. The feedback network of pneumatic pressure transducer (PPT) 36 and high pass filter 34 should be stable and modifiable. In a preferred embodiment, PPT 36 comprises a piezoelectric integrated circuit pressure sensor such as Model SX05 manufactured by Sensym of Sunnyvale, Calif. This PPT responds to DC pressures of up to 350 mmHg and has a frequency response that begins to roll off at about 10,000 Hertz. It will be appreciated that such a piezoelectric silicon diaphragm will yield a very stable transducer. HPF 34 preferably comprises a fourth order Bessell filter. A preferred error amplifier 30 comprises a Linear Technologies, LT1013. Simulator control console 14 will comprise any known suitable membrane keyboard and suitable display means such as LCD or LED types. Microcomputer 41 and PWS 28 preferably comprise a commercially available Motorola 68HCll in conjunction with a suitable digital-to-analog (D/A converter). It will be appreciated that both HPF 34 and error amplifier 30 may comprise software as opposed to electronic hardware.

The purpose of the Pneumatic Pulse Generator (PPG) (and the Hydraulic Pulse Generator which will be discussed hereinafter) is to transform the electrical pulse waveform into an equivalent fluidic pressure signal. Thus, the PPG is a type of transducer since it converts energy from one form (electrical) to another (mechanical).

While the PPG may consist of many different embodiments, in the preferred embodiment, this energy conversion is accomplished as a two step process: First, an electro-mechanical linear motion transducer converts the electrical signal into a corresponding mechanical displacement. Second, this displacement is converted to a fluidic pressure by the piston in a pneumatic or hydraulic cylinder.

While the linear motion transducer could consist of a variety of devices such as a conventional "snap-acting" linear solenoid or a digital linear actuator (a stepper motor fitted with a lead screw), the preferred embodiment is a "proportional" linear solenoid such as a Lucas Ledex Model PS-16. The PS-16 provides a mechanical displacement, or stroke, that is proportional to input current. To convert this displacement to a pressure change, the present invention couples the plunger, or shaft, of the PS-16 to the shaft of a suitable pneumatic/hydraulic cylinder such as a Clippard Model 7SD-1 miniature cylinder. The cylinder functions like a piston pump in reverse: Displacement of the cylinder shaft moves the cylinder piston against the fluid (either air or liquid) thereby compressing the fluid and converting the displacement into a fluid pressure change.

Operation of the simulator of the present invention begins by selecting the desired MAP, systolic and diastolic BP and heart rate on the control console 14. Pneumatic cuff 18 of the monitor-under-test 20 is then wrapped around simulator body 12 and the measurement cycle begins. Assuming the monitor has an integral pump, it inflates the cuff to the initial pressure and then begins deflating the cuff and looking for pressure pulses. Simulator 10 senses the cuff pressure via tubing 22 and 27; and derives corresponding pulse amplitudes from the selected envelope pattern. Pressure pulses having these amplitudes are generated at the desired heart rate and are transmitted to the cuff 18 via tubing 23. Thus, as monitor 20 deflates cuff 18, the pulses it measures will be those carefully synthesized by simulator 10 in order to create the desired envelope pattern. A two-way "dialogue" between simulator 10 and monitor 20 takes place: monitor 20 controls the DC cuff pressure at any given time and simulator 10 senses it and responds with oscillometric pulses whose amplitude is a function of the DC cuff pressure.

Figure 5B:
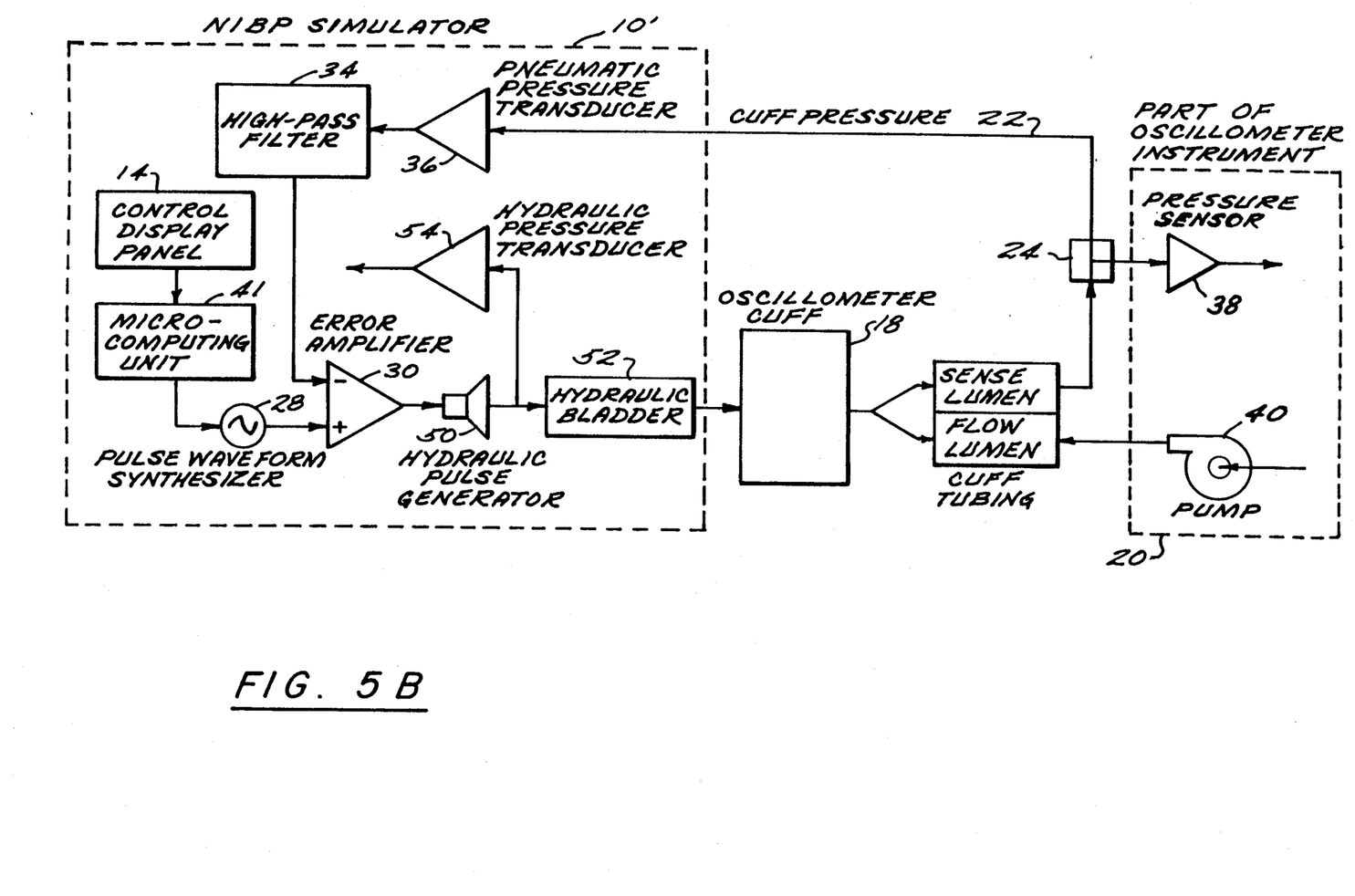
FIG. 5B is a schematic of an alternative embodiment of the present invention.
Figure 5C:
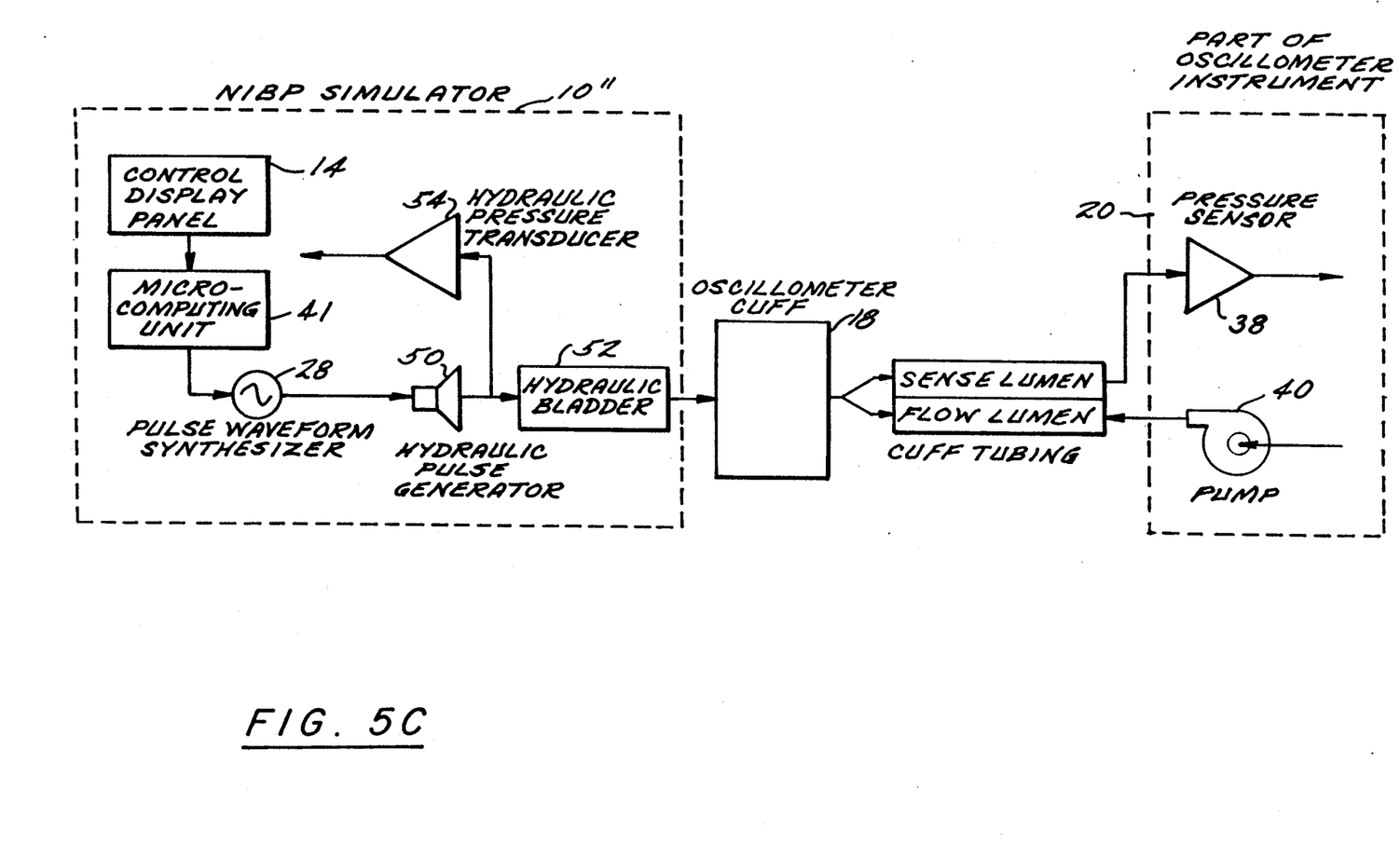
FIG. 5C is a schematic of still another alternative embodiment of the present invention.

FIGS. 5B and 5C depict less preferred embodiments of the NIBP simulator of the present invention with structure corresponding to that found in FIG. 5A having the same reference numeral. The simulator 10' of FIG. 5B differs from FIG. 5A in that the pulse waveforms are hydraulically generated rather than pneumatically generated. In FIG. 5B, pulse waveform synthesizer 28 delivers signals to a hydraulic pulse generator 50 which communicates with a hydraulic bladder 52. Hydraulic bladder 52 thus acts to deliver simulated pressure pulses to oscillometer cuff 18. Hydraulic pressure transducer 54 senses the DC component or mean pressure from bladder 52 while the cuff 18 senses the AC component or pulse wave form from bladder 52.

FIG. 5B retains the important "servo loop" feature of FIG. 5A. That is, the embodiment of FIG. 5B is a closed-looped system which incorporates feedback to sense and control the pulse waveform at the output of tubing 22. In the FIG. 5B embodiment, the connection between simulator 10' is tapped at tubing 22. The tapped pressure is sensed by the pneumatic pressure transducer 36, its DC component is stripped by the high-pass filter 34 and the resulting AC pressure signal is fed back to the error amplifier 30. The error amplifier 30 then compares the actual pressure signal with the desired signal from pulse wave form synthesizer 28 and drives the hydraulic pulse generator 50 with a correction signal.

The simulator 10" of FIG. 5C depicts still another embodiment o the present invention which is less preferred than either the embodiments of FIGS. 5A or 5B. Basically, the FIG. 5C embodiment is an open-looped simulator, that is, FIG. 5C is analogous to the FIG. 5B embodiment without the "servo-loop" feature. This FIG. 5C embodiment of simulator 10" includes a hydraulic pulse generator 50, hydraulic pressure transducer 54 and hydraulic bladder 52. As in FIG. 5B, bladder 52 is wrapped about cylindrical housing 12 and the oscillometer cuff 18 is wrapped about bladder 52. During a simulated measurement cycle, the mean or DC pressure in the cuff is transferred to the bladder 52 where it can be sensed by transducer 54. Meanwhile, the pulse or AC pressure waveforms synthesized by generator 50 are transmitted via bladder 52 to cuff 18.

FIG. 5C includes the significant feature of the present invention wherein the simulator 10" is completely "non-invasive" to the oscillometer-under-test. This allows for testing of the oscillometer without the need for dismantling or otherwise disturbing the oscillometer. Unfortunately, while this embodiment is indeed non-invasive; it does not contain the important "servo-loop" feature which adversely impacts on the accuracy of the simulator as discussed above.

Another important feature of the present invention is the physiological correctness of the synthesized pulse waveforms and oscillometric envelope. Because the pulse waveforms are physiologically correct, simulator 10 can provide a valid "test suite" to evaluate the effectiveness of pulse detection algorithms. In fact, measured amounts of noise (of various types) could be superimposed on the pulses to allow algorithm behavior to be studied in a controlled manner.

While the physiologically correct synthesized pulse waveforms and oscillometric envelope may be determined by any desired method, a preferred technique for obtaining such data is through a clinical study such as follows.

The primary concern in this empirical (clinical) study is to collect waveforms that are representative of what an oscillometric BP monitor will sense. The clinical data collection set-up for characterizing the cuff pulse waveforms is presented in FIG. 6. Direct arterial pressures are recorded from the left (preferably) radial artery and, when possible, from the aorta. The invasive measurements are obtained via catheter-tip pressure transducers (Medical Measurements, Hakensack, N.J.) in order to eliminate the artifact often caused by "catheter whip". The transducer signals are fed to the patient monitor (Model VR-16, Honeywell E for M, Pleasantville, N.Y.) which will isolate, amplify and display the pressures. The patient monitor also feeds the two pressure signals to the Analog I/O Board (Model DT2808, Data Translation, Marlboro, Mass.) where they are digitized to 12 bit resolution at 50 samples/second and stored in the hard disk of the microcomputer (Portable II, Compaq, Richardson, Tex.). The microcomputer also displays the acquired digitized signals in order to provide a quality check of the recordings.

A Critikon Dynamap cuff (Model 1845, Critikon, Tampa, Fla.) sized to the patient according to AHA guidelines (cuff width approximately 40% of arm circumference) is applied to the right arm (contralateral to the catherized arm). The standard Dynamap 8 foot, dual-lumen cuff tube is used to connect the cuff to the pressure transducer within the oscillometer interface (custom built).

The output of this transducer is split into DC and AC components by filters in the oscillometer interface. It is essential that the bandwidth of the AC component is as wide as is necessary in order not to distort the pulse waveform.

The DC and AC cuff pressure signals are then digitized to 12 bit resolution by the analog I/0 board. The AC pressure component is sampled at 100 samples/-second (assuming this is consistent with the bandwidth needed) while the DC component is sampled at 10 samples/second; both digitized signals are stored in the hard disk.

The flow-lumen of the cuff tubing connects the cuff to the inflation pump and deflation valves with the oscillometer interface. The microcomputer sends signals to the oscillometer interface to control the cuff inflation, deflation and venting. The data collection and cuff control software is written using the ASYST scientific data acquisition and analysis software package.

The following protocol is used to record the four signals:

1) Enter patient clinical history into a database via the microcomputer.
2) Measure the brachial pressure in each arm via manual auscultation.
3) Catheterize the patient and verify the stability and quality of the direct pressure signal(s) on the patient monitor display and on the PC.
4) Apply the arm cuff to the subject and ask him/her to remain quiet.
5) Initiate a "test inflation" cycle via the PC and the oscillometer interface and verify the stability and quality of the two indirect pressure signals on the PC. (This will inflate the cuff to about 100 mmHg for about 10 sec.).
6) Initiate a "data collection" cycle and record the four signals for 60 seconds. A data collection cycle consists of a rapid inflation to well above systolic pressure, cuff deflation until pulses occur, deflation at 5 mmHg steps and pausing for 2 cardiac cycles and rapid venting after pulses disappear. A 60 second cycle avoids problems related to venous pooling.

This procedure is repeated four times for each the subjects. Each recording session generates a data file, 25 KiloBytes long. These files are stored on the data collection microcomputer's hard disk and transferred periodically via floppy disk and/or modem, to the signal processing workstation at another location. The data files (approximately 8 megabytes in total) are archived on the workstation hard drive and used for the data analysis phase of the project.

Next, the data is analyzed. The object of the data analysis is to identify the typical characteristics of the pulse waveform and oscillometric envelope in subjects with and without peripheral vascular disease. The characteristics that are analyzed are listed below:

Pulse waveform characteristics:
width and duty cycle
rise time
fall time
energy (area under the curve)
maximum and minimum slopes
waveshape indices The last item needs clarification: An indication of the general similarity of waveform shapes at different mean cuff pressures is obtained by computing the autocorrelation function (ACF) of the pulse waveform for a given subject during a single data collection cycle. To access waveform shape similarity at the same mean cuff pressures for a given subject, all pulse waveforms collected for a given mean cuff pressure will be "waveform summed". The average of the summed waveforms are used as the template or "kernel" to compute a crosscorrelation function (XCF) that will indicate waveshape similarities. Finally, the waveshapes for pulses at the same cuff pressure in different subjects are compared by computing the XCF of each subject's template waveform and the template of every other subject.

Four envelope characteristics include:
(1) location of arterial diastolic, mean and systolic pressures
(2) characteristic ratios for systolic, diastolic and mean
(3) characteristic slopes for systolic, diastolic and mean
(4) waveshape indices The waveshape indices for the envelope will be obtained similarly to those for the pulse waveform except that, obviously, the ACF cannot be computed.

The signal analysis is performed by software written in ASYST, which provides interactive signal plotting, numerical analysis and statistics. The software analyzes each set of four acquired signals as follows:

1) Each of the four signals is displayed and the signal quality is checked visually.
2) For the arterial pressure signal(s), the following parameters are computed on a beat-to-beat basis and their mean and standard deviations calculated:
   mean pressure
   systolic pressure
   diastolic pressure
   pulse pressure (systolic-diastolic)
   systolic fraction ("duty cycle")
   waveform coefficient ([mean-dia]/[sys-dia])
3) The pulse waveform parameters listed above (except for the waveshape indices) are computed for all the pulses collected at the various mean pressure values.
4) The envelope parameters (except for the waveshape indices) are computed from the mean values computed in step 2).

This procedure is repeated for each of the four sets collected for every patient. If the pulse and envelope parameters derived from these sets appear to be consistent they are averaged to form the patient parameter set. If not, the patient data will be disregarded. This entire process is repeated for the data from each patient and then the waveshape indices are computed.

Multi-linear regression and standard statistical analysis techniques are used to correlate the dependent, oscillometric variables—the pulse and envelope parameters—with the independent, physiological variables—the arterial BP parameters and the cardiovascular condition of the subject.

Physiologically-correct pulse waveforms and oscillometric envelopes (derived from the clinical testing described in detail above) allows for valid testing of any oscillometric monitor regardless of the particular method used to determine systolic and diastolic pressures which is not possible with prior art devices such as that disclosed in previously mentioned U.S. Pat. No. 4,464,123 to Glover et al. The Glover et al device uses an oscillometric envelope which is a mathematically convenient, three segment linearized function; and can only be used with the oscillometer of a particular manufacturer for obtaining meaningful test results. For example, another manufacturer may have selected different fractional relationships (which provide the best accuracy for that specific oscillometer implementation); or, an entirely new approach (such as the aforementioned derivative method) not based on fractional relations may be employed by a given manufacturer. In contrast, the present invention, because it recreates the true physiological waveforms, will provide valid results with either of these latter two cases, whereas the device of Glover et al would be useless.

The NIBP simulator in accordance with the present invention allows complete dynamic evaluation of any monitor (regardless of manufacturer) under conditions that emulate an actual measurement by using a novel preferably closed loop system to synthesize physiologically correct, pneumatic pulse waveforms and oscillatory envelopes in order to allow dynamic performance evaluation of any oscillometric monitor.

The simulator of this invention will improve the accuracy of oscillometric BP monitors currently used and it will encourage refinements in oscillometric technology that will lead to more accurate BP monitor designs. Specifically, it will provide:

1) a standardized signal source for comparing oscillometers from any manufacturer;
2) a means for independent validation of oscillometer performance claims;
3) a quick, objective method for clinical staff to verify oscillometer performance without placing a service call to biomedical engineering;
4) a test fixture that will simulate motion artifact and other types of noise in order to evaluate oscillometer performance under adverse conditions;
5) a method to analyze the accuracy of the different systolic and diastolic blood pressure prediction algorithms used in oscillometers; and
6) a data base of clinically derived oscillometric pulse waveforms and envelopes representing various cardiovascular conditions that can be used to develop improved algorithms for pulse detection, noise reduction and systolic/diastolic prediction.

As is clear from FIG. 5A, the simulator of the present invention may be used without oscillometer cuff 18. In this case, a reservoir would be provided in simulator 10 to act as a container for retaining fluid which would have been received in cuff 18. Alternatively, simulator 10 could include suitable venting means which would vent that fluid normally delivered to the cuff. Thus, the simulator of the present invention could, in effect, bypass the cuff 18 and concentrate solely on the accuracy and operation of the oscillometer under test.

While an important feature of the present invention is to allow for evaluation of the instrument (electronic) section of an NIBP monitor, another application of this invention is to allow evaluation of the oscillometer cuff and cuff tubing. Cuff and tubing properties of interest include:

1. the transfer function (i.e., the input/output response);
2. the impedance (pressure change per flow rate change);
3. stiffness (pressure change per volume change);
4. compliance (flow rate change per pressure change per second); and
5. hermetic integrity (airtightness).

It will be apPreciated that the impedance, stiffness and compliance are the pneumatic analogs of, respectively, the electrical quantities resistance, capacitance and inductance.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An apparatus for evaluating the performance characteristics of an oscillometric blood pressure monitor which has a pressure sensor and a pump and in which cuff pressure pulse signals are generated when it is monitoring the blood pressure of a human subject, comprising:

pulse waveform synthesizer means for synthesizing pulses with predetermined waveforms that have shapes, slopes, amplitudes and rates that are substantially the same as the corresponding parameters of cuff pressure pulses taken from particular human subjects and are therefore physiologically correct;

pulse generator means for converting said synthesized pulses to a pressure signal of pulses which have substantially the same parameters and physiological correctness as the synthesized pulses; and means for enabling said pressure signal to be sensed by the pressure sensor in the monitor so that when the pump applies pressure, the monitor will generate cuff pressure pulse signals which have shapes, slopes, amplitudes and rates that are substantially the same as would be generated by the monitor when used to monitor the blood pressure of the human subjects whose cuff pressure pulses are synthesized.

2. The apparatus of claim 1 including:

computer means which store blood pressure data taken from human subjects, such data including the waveform parameters of shape, slope, amplitude and pulse rate of the cuff pressure waveforms of the subjects, said computer means being capable of delivering cuff pressure waveforms which incorporate said parameters to the pulse waveform synthesizer means.

3. The apparatus of claim 2 including:

control means for selecting from said computer means a predetermined cuff pressure pulse waveforms.

4. The apparatus of claim 1 wherein the pump generates pressure having a DC component and wherein said pulse generator means generates pressure having an AC component, said apparatus further including:

means for sensing the cuff pressure;

means communicating with said sensing means for separating the DC and AC components of the sensed pump pressure; and means responsive to the separating means for comparing the AC component with the pulses from the pulse waveform synthesizer means and delivering a correction signal to the pulse generator means.

5. A simulator for testing an oscillometric blood pressure monitor, said monitor being attachable to a living subject for determining the blood pressure of the subject and having fluid pressure means in which the pressure can be varied in the taking of blood pressure measurements, and further having electrical means responsive to the fluid pressure means for generating cuff pressure pulses of characteristic shape from which the mean, systolic and diastolic blood pressure of the subject are measured, comprising:

means for producing a series of fluid pressure pulses which have waveforms with shapes, slopes and areas substantially the same as the waveforms of the cuff pressure pulses of living subjects and which incorporate the mean systolic and diastolic pressure and pulse rate values of the subject, whereby the fluid pressure waveforms are physiologically correct; and means for transmitting the fluid pressure pulses to the fluid pressure means of the monitor so that when the monitor is not attached to a living subject and the pressure is varied by the fluid pressure means, the electrical means will generate cuff pressure pulses having substantially the same characteristic shape as that generated when the monitor is checking the blood pressure of a living subject, whereby the monitor can be tested by comparing the values of blood pressure as measured by the monitor with the values incorporated into the fluid pressure waveforms.

6. A simulator for testing an oscillometric blood pressure monitor in which a fluid pressure source applies pressure to an inflatable cuff attached to a living subject and a transducer senses the pressure in the cuff and generates an electrical signal having cuff pressure pulses of characteristic shape from which blood pressure values of the living subject are determined, comprising:

electronic means which store in digitized form data on cuff pressure waveforms collected from living subjects so that the stored data defining a particular waveform are substantially the same as the data defining the actual waveform collected from the corresponding living subject and are thereby physiologically correct, said data including the shapes, amplitudes and pulse rates of the waveforms;

means for selecting stored waveforms by selecting a pulse rate and amplitudes equal to desired systolic, mean and diastolic blood pressures thereby to establish predetermined values for testing the monitor;

means responsive to the selected waveforms for synthesizing analog fluid pressure pulses having waveforms that incorporates the predetermined values of the stored waveforms and is thus physiologically correct; and means for transmitting the fluid pressure pulses to the cuff so that when said pressure source applies pressure to the cuff when the cuff is not attached to a living subject, the transducer will generate cuff pressure pulse signals of substantially the same shape as that generated when the monitor is checking the blood pressure of a living subject whereby the values of blood pressure as measured by the monitor can be compared with the predetermined values to test the monitor.

7. The simulator of claim 6 wherein the electronic means stores data collected from human subjects having a variety of cardiovasular conditions so that said selecting means can select waveforms representative of particular cardiovascular conditions to enable testing of the monitor ovar a range of types of human blood pressure conditions.

8. A simulator for evaluating the accuracy of an oscillometric blood pressure monitor attachable to a human subject for determining blood pressure of the subject, said monitor having fluid pressure means in which the pressure is increased and decreased during the taking of the blood pressure of a human subject, and having electrical means for generating cuff pressure pulse signals of characteristic shape from which the mean, systolic and diastolic blood pressures and the pulse rate of the human subject are determined, comprising:

electronic means which store in digitized form data on cuff pressure waveforms collected from human subjects so that the stored data defining a particular waveform are substantially the same as the data defining the actual waveform collected from the corresponding human subject and are thereby physiologically correct, said data including the shapes, amplitudes and pulse rates of the waveforms;

means for selecting a stored waveforms by selecting a pulse rate and amplitudes equal to desired systolic, mean and diastolic blood pressures thereby to establish predetermined values for testing the monitor;

means responsive to the selected waveforms for synthesizing analog fluid pressure pulses having a waveforms that incorporates the predetermined values of the stored waveforms and is thus physiologically correct; and means for transmitting the fluid pressure pulses to the fluid pressure means of the monitor so that when the monitor is not attached to a human subject and the pressure is increased and decreased by the fluid pressure means, the electrical means will generate cuff pressure pulse signals having substantially the same characteristic shape as that generated when the monitor is checking the blood pressure of a human subject, whereby the values of blood pressure as measured by the monitor can be compared with the predetermined values to evaluate the accuracy of the monitor.

9. An apparatus for evaluating the performance of an oscillometric blood pressure monitor having a fluid pressure system including a pressure source and a pressure sensor, comprising:

means for synthesizing predetermined waveforms;

pulse generator means for converting said predetermined waveforms to a pressure signal;

means for transmitting said signal to the pressure system in an oscillometric blood pressure monitor to produce a combined pressure signal having AC and DC components when there is an applied pressure in the system; and means responsive to the combined signal for extracting its AC component and for delivering to said pulse generator means a correction signal based on a comparison of the waveforms of said AC component and said predetermined waveforms.

10. A simulator for testing an oscillometric blood pressure monitor which has fluid pressure means for varying the pressure during the taking of blood pressure measurements and which also has electrical means responsive to the fluid pressure means for generating cuff pressure pulse signals from which the blood pressure of the subject is measured, comprising:

means for producing a series of fluid pressure pulses which have predetermined waveforms;

means for transmitting the fluid pressure pulses to the fluid pressure means of the monitor so that when the fluid pressure means varies the pressure a combined fluid pressure signal having AC and DC components is generated;

means for separating the AC component from the combined signal; and means for developing a correction signal based on a comparison of the waveform of the AC component and a preselected waveform and for using the correction signal to modify the fluid pressure pulses at the producing means.

11. A simulator for testing an oscillometric blood pressure monitor which has fluid pressure means for varying the pressure during the taking of blood pressure measurements and which also has electrical means responsive to the fluid pressure means for generating cuff pressure pulse signals from which the blood pressure of the subject is measured, comprising:

means for producing a series of fluid pressure pulses which have predetermined waveforms that have shapes, slopes, amplitudes and rates which are substantially the same as the corresponding parameters of the cuff pressure waveforms of living subjects from whom blood pressure data has been collected;

means for transmitting the fluid pressure pulses to the fluid pressure means of the monitor so that when the fluid pressure means varies the pressure, a combined fluid pressure signal having AC and DC components is generated;

means for separating the AC component from the combined signal, said AC component having a first waveform; and means for developing a correction signal based on a comparison of said first waveform of the AC component and a preselected waveform, said preselected waveform having first parameters associated therewith, and means for using the correction signal to modify the fluid pressure pulses at the producing means so that said electrical means of the monitor will generate a substantially distortion free cuff pressure pulse signal which incorporates said first parameters of said preselected waveform.

12. An apparatus for evaluating the performance characteristics of an oscillometric blood pressure monitor having a pressure sensor and a pump comprising:

pulse waveform synthesizer means for synthesizing predetermined waveforms to define a predetermined oscillometric envelope pattern;

pulse generator means for converting said predetermined pulse waveforms to a pressure signal capable of being sensed by the pressure sensor in the oscillometric blood pressure monitor;

pressure transducer means for sensing pressure produced by the pump in the oscillometric blood pressure monitor;

high pass filter means electrically communicating with said pressure transducer means, said high pass filter means adapted to separate the DC and AC components from the sensed pump pressure; and error amplifier means for receiving the AC component from said high pass filter means, said AC component having a first waveform, said error amplifier means comparing a preselected waveform with said first waveform of said AC component sensed by said pressure transducer means and delivering a correction signal to said pulse generator means.

13. In a method for testing an oscillometric blood pressure monitor which produces a characteristic oscillometric envelope signal from which systolic, mean and diastolic blood pressures and pulse rate of a living subject are determined when the monitor is connected to the subject, said method involving the transmission of simulated cuff pressure pulses to the monitor, including the steps of:

collecting blood pressure and cuff pressure data from living subjects which includes blood pressure waveforms with their unique parameters of shapes, slopes, areas, rise and fall times, rates and amplitudes, and obtaining systeolic, mean, diastolic pressures and pulse rate via direct measurement, so that the data define physiologically correct waveforms of the subjects;

electronically storing the collected blood pressure data;

selecting a desired waveform for testing such a monitor by selecting certain systolic, mean and diastolic pressures and a pulse rate; and converting the selected waveform into fluid pressure pulses having substantially the same waveform and incorporating substantially the same parameters as the electronically stored waveform, for transmission to such a monitor so that the monitor will produce its characteristic oscillometric envelope signal incorporating said unique parameters in substantially the same manner as if the monitor were being used to monitor the blood pressure of the living subject from whom the stored data was collected.

14. In a method for testing an oscillometric blood pressure monitor which produces a characteristic oscillometric envelope signal from which systolic, mean and diastolic blood pressures and pulse rate of a living subject are determined when the monitor is connected to the subject, said method involving the tansmission of simulated cuff pressure pulses to the monitor, including the steps of:

collecting blood pressure and cuff pressure data from living subjects which includes cuff pressure waveforms with their unique parameters of amplitudes, shapes, slopes, areas, rise and fall time, and rates, so that the data define physiologically correct waveforms of the subjects;

electronically storing the collected blood pressure data;

selecting a desired waveform for testing such a monitor by selecting certain systolic, mean and diastolic pressures and a pulse rate;

converting the selected waveform into fluid pressure pulses having substantially the same waveform and incorporating substantially the same parameters as the electronically stored waveform for transmission to such a monitor to generate a combined pressure signal having AC and DC components;

developing a correction signal based on said AC component; and applying the correction signal so as to counteract distortion in the fluid pressure pulses.

15. A method for evaluating the performance characteristics of an oscillometric blood pressure monitor having a pressure sensor and a pump comprising the steps of:

synthesizing predetermined waveforms to define a predetermined oscillometric envelope pattern;

converting said predetermined pulse waveforms to a pressure signal capable of being sensed by the pressure sensor in the oscillometric blood pressure monitor;

sensing pressure in the oscillometric blood pressure monitor, said pressure being sensed by pressure transducer means;

using high pass filter means to separate the DC and AC components from the sensed pump pressure; and using error amplifier means for receiving the AC component from said high pass filter means, said AC component having a first waveform, said error amplifier means comparing a preselected waveform with said first waveform of said AC component sensed by said pressure transducer means and delivering a correction signal to said pulse generator means.

* * * * *